(12) United States Patent
Al-Khalidy et al.

(10) Patent No.: US 7,349,521 B2
(45) Date of Patent: Mar. 25, 2008

(54) COMPRESSION PADDLE FOR MAMMOGRAPHY SYSTEMS

(75) Inventors: Abdulrahman Abdallah Al-Khalidy, Latham, NY (US); Ajay Kapur, New York, NY (US); Jeffrey Wayne Eberhard, Albany, NY (US); Henri Souchay, Versailles (FR); Philip Alexander Shoemaker, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/257,837

(22) Filed: Oct. 25, 2005

(65) Prior Publication Data

US 2006/0262899 A1    Nov. 23, 2006

Related U.S. Application Data

(60) Provisional application No. 60/682,777, filed on May 19, 2005.

(51) Int. Cl.
*A61B 6/04* (2006.01)

(52) U.S. Cl. ...................................................... 378/37

(58) Field of Classification Search .................. 378/37, 378/208
See application file for complete search history.

(56) References Cited

U.S. PATENT DOCUMENTS

| 4,875,478 A | * | 10/1989 | Chen ........................... 600/429 |
| 4,943,986 A | * | 7/1990 | Barbarisi ....................... 378/37 |
| 5,199,056 A | * | 3/1993 | Darrah ........................... 378/37 |
| 6,876,879 B2 | * | 4/2005 | Dines et al. ................. 600/427 |
| 2004/0125912 A1 | * | 7/2004 | Wikander ..................... 378/37 |
| 2004/0218727 A1 | | 11/2004 | Shoenfeld |
| 2005/0008117 A1 | * | 1/2005 | Livingston ................... 378/37 |
| 2005/0063509 A1 | | 3/2005 | Defrellas et al. |

* cited by examiner

*Primary Examiner*—Edward J. Glick
*Assistant Examiner*—Anastasia S. Midkiff
(74) *Attorney, Agent, or Firm*—Jenifer E. Haeckl; Jason K. Klindtworth

(57) ABSTRACT

Disclosed herein is a compression paddle comprising a paddle base 12; and a paddle wall 20 comprising a first side-wall 22; and a second side-wall 24; wherein the first side-wall 22 and/or the second side-wall 24 are disposed upon the paddle base 12 and inclined with respect to the paddle base 12 at an angle that is effective to permit an x-ray beam uninterrupted access to an object of interest located on an opposing side of the paddle base 12 from an x-ray source when an angle between a central axis of the x-ray beam and a vertical taken at an inner surface of the first side-wall 22 and/or the inner surface of the second side-wall 24 is about 15 degrees to about 75 degrees.

10 Claims, 6 Drawing Sheets

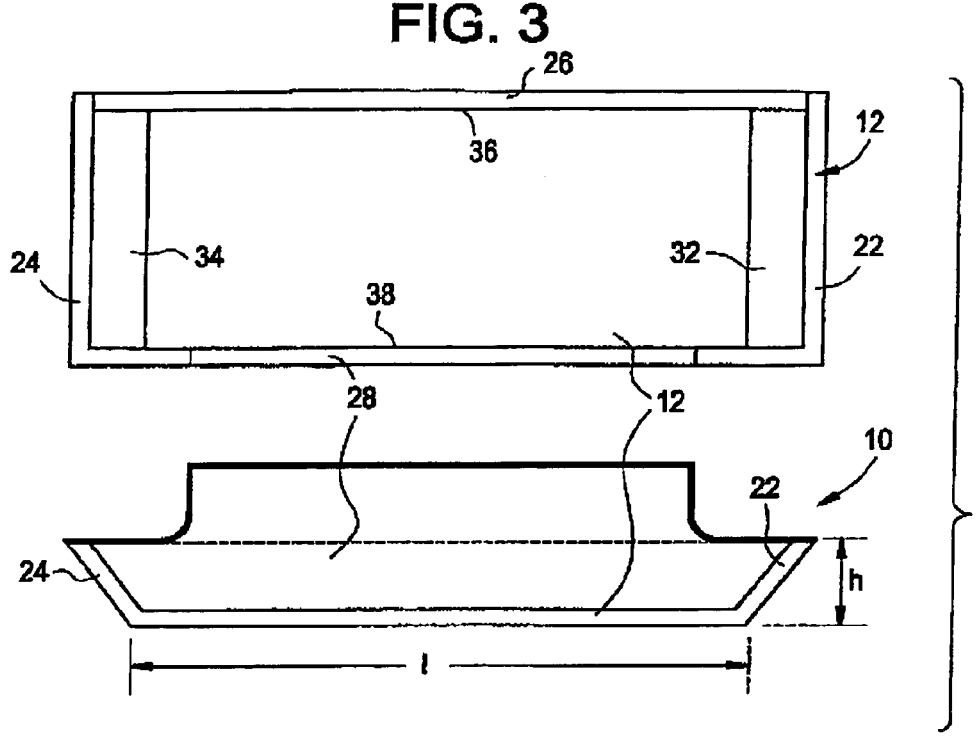
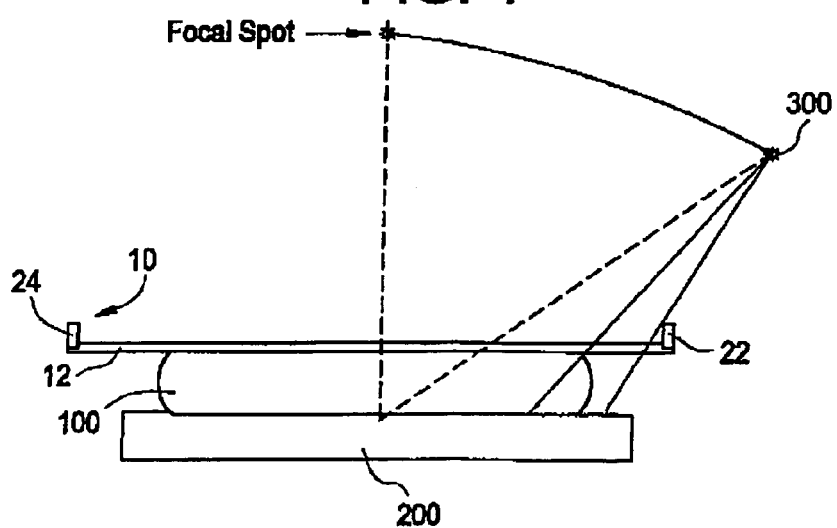

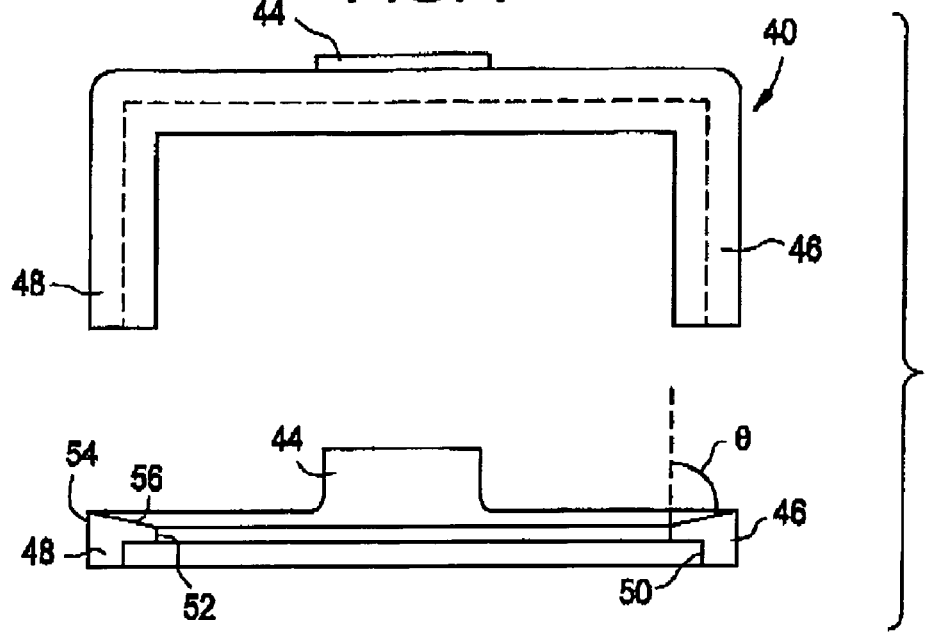
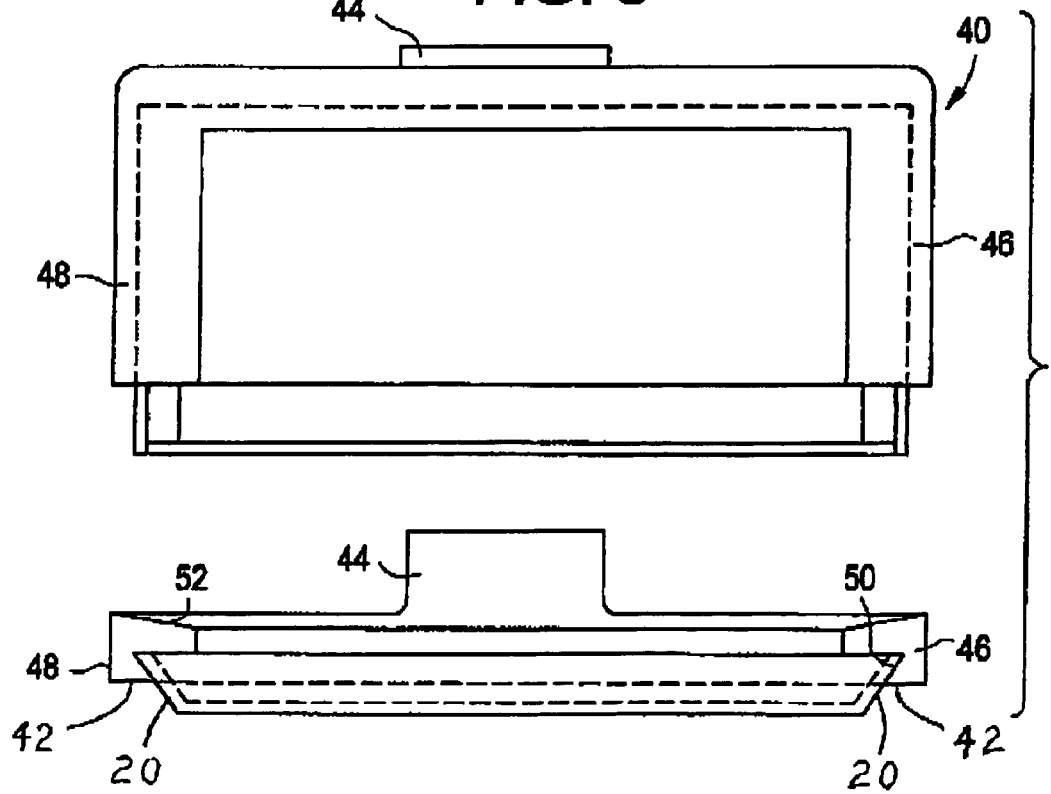

COMPRESSION PADDLE FOR MAMMOGRAPHY SYSTEMS

CROSS-REFERENCE TO RELATED APPLICATIONS

This application claims the benefit of U.S. Provisional Application Ser. No. 60/682,777 filed May 19, 2005, which is fully incorporated herein by reference.

STATEMENT REGARDING FEDERALLY SPONSORED RESEARCH AND DEVELOPMENT

This invention was made with Government support under contract numbers MDA9050210012 awarded by US Army Medical Research Acquisition Activity and MDA905-00-10041 awarded by National Institute of Health (NIH). The Government has certain rights in the invention.

BACKGROUND

This disclosure relates to breast compression paddles for use in mammography systems, including standard and tomosynthesis mammography systems.

Compression paddles for mammography have shapes that are generally optimized for patient comfort and for ease of positioning the breast during mammography. However, this optimization results in a compression paddle that has high lateral walls and a rigid metal frame, which is adverse to large angle (e.g., a total scanning angle of about 30 degrees to about 120 degrees) tomosynthesis imaging.

Tomosynthesis is a technique that allows the reconstruction of tomographic planes on the basis of the information contained in a series of projections acquired from a series of angular viewpoints about the target object (breast). They need not be regularly spaced, numerous, or arranged in any regular geometry. The tomosynthesis technique can provide improved spatial differentiation of nearby tissues at very high resolution comparable with projection 2D imaging. Tomosynthesis permits this to be accomplished while subjecting the patient to limited amounts of radiation.

The series of angular viewpoints about the breast (hereinafter "the object of interest") can include angles of about ±15 degrees to about +/−60 degrees. However, the high lateral walls and the metal frame of the compression paddle obstruct the path of the x-ray beam and consequently a shadow from the high lateral walls and the metal frame is superimposed upon information obtained from the breast, which adversely affects the images of the breast. This obstruction can be clearly seen in the FIG. 1. FIG. 1 reflects a view of a compression paddle design that obstructs the x-rays during tomosynthesis imaging. As can be seen from the FIG. 1, a breast 100 is disposed between the compression paddle 10 and the detector 200 of the x-ray device. The compression paddle 10 lies between the detector 200 and an x-ray source 300. The compression paddle 10 comprises a paddle wall 20 and a paddle base 12. The paddle base 12 is fixedly attached to the paddle wall 20. In the depicted configuration, a largest vertical dimension of the paddle wall 20 is perpendicular to the paddle base 12. A bracket (not shown) provides support for the compression paddle 10 and permits the compression paddle to be displaced about a pivot point on the x-ray device. The pivot point is generally that point at which the bracket is in mechanical communication with the x-ray device. As can be seen from the FIG. 1, as the x-ray source 300 is rotated during tomosynthesis, at certain angles, the paddle wall obstructs the x-rays, and a shadow of the paddle wall, is projected onto the detector. This shadow is superimposed upon images of the breast, which is undesirable. Although reconstruction techniques may partially remove the above shadows, residual artifacts may be present in the images.

It is therefore desirable to have a compression paddle that does not obstruct images of the breast, while at the same time maintaining optimal patient comfort and permitting ease of positioning.

SUMMARY

Disclosed herein is a compression paddle comprising a paddle base; and a paddle wall comprising a first side-wall; and a second side-wall; wherein the first side-wall and/or the second side-wall are disposed upon the paddle base and inclined with respect to the paddle base at an angle that is effective to permit an x-ray beam uninterrupted access to an object of interest located on an opposing side of the paddle base from an x-ray source when an angle between a central axis of the x-ray beam and a vertical taken at an inner surface of the first side-wall and/or the inner surface of the second side-wall is about 15 degrees to about 75 degrees.

Disclosed herein too is a compression paddle comprising a paddle base; and a paddle wall comprising a first side-wall; and a second side-wall; wherein the first side-wall and/or the second side-wall are disposed upon the paddle base and have a height that is effective to permit an x-ray beam uninterrupted access to an object of interest located on an opposing side of the paddle base from an x-ray source when an angle between a central axis of the x-ray beam and a vertical taken at an inner surface of the first side-wall and/or the inner surface of the second side-wall is about 15 degrees to about 75 degrees.

Disclosed herein too is a bracket for use in an x-ray device comprising a groove for fixedly attaching or matingly engaging a compression paddle; a first arm; and a second arm; each having the groove disposed therein; wherein the first arm and the second arm extend from a central portion of the bracket, and wherein the first arm and the second arm comprise angulated upper surfaces that permit an x-ray beam uninterrupted access to an object of interest located on an opposing side of the paddle base from an x-ray source when an angle between a central axis of the x-ray beam and a vertical taken at an inner surface of the first arm and/or the inner surface of the second arm is about 15 degrees to about 75 degrees.

Disclosed herein too is a method comprising disposing upon an object of interest a compression paddle 10 comprising a paddle base 12; and a paddle wall 20 comprising a first side-wall 22; and a second side-wall 24; wherein the first side-wall 22 and/or the second side-wall 24 are disposed upon the paddle base 12 and inclined with respect to the paddle base 12 at an angle that is effective to permit an x-ray beam uninterrupted access to an object of interest located on an opposing side of the paddle base 12 from an x-ray source when an angle between a central axis of the x-ray beam and a vertical taken at an inner surface of the first side-wall 22 and/or the inner surface of the second side-wall 24 is greater than or equal to about 15 degrees to about 75 degrees; and obtaining an image of the object of interest.

Disclosed herein too is an x-ray device that employs the compression paddle and the bracket.

DESCRIPTION OF FIGURES

With reference now to the Figures, wherein like parts are numbered alike,

FIG. 3 is a depiction of an upper view and a side view of an exemplary compression paddle 10 that comprises angulated side-walls; the compression paddle also has an increased height front-wall;

FIG. 4 is a schematic depiction illustrating that a compression paddle 10 with appropriately reduced height side-walls 22, 24 does not obstruct the x-rays during imaging;

FIG. 7 is depiction of an exemplary bracket 40 for supporting the compression paddle 10;

FIG. 8 is a depiction of a plan view and a side view of an exemplary bracket 40 that comprises a first arm 46 and a second arm 48 each of which have a groove 50 disposed therein; the groove 50 provides frictional communication for a compression paddle 10 that contacts the bracket 40;

DETAILED DESCRIPTION

Figure 1:
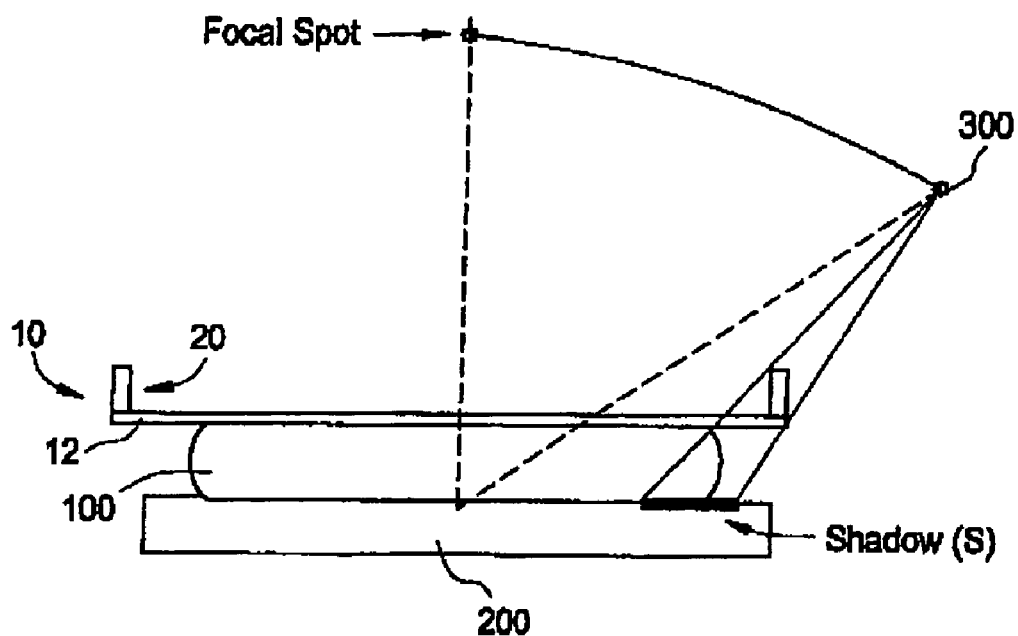
FIG. 1 is a depiction of a currently commercially available compression paddle 10 design that obstructs the x-rays during tomosynthesis imaging.

In the following description, like reference characters designate like or corresponding parts throughout the several views shown in the figures. It is also understood that terms such as "top", "bottom", "outward", "inward", and the like are words of convenience and are not to be construed as limiting terms. It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity).

Disclosed herein is a compression paddle having two or more side-walls that do not obstruct an x-ray beam during mammography. Disclosed herein too is a bracket that is fixedly attached to the compression paddle to provide the compression paddle with support. The arms of the bracket are designed to be angulated or beveled and to have a reduced height so as not to obstruct an x-ray beam during mammography. In one embodiment, the compression paddle can be combined with the bracket such that the combination does not obstruct an x-ray beam during mammography. The compression paddle and the bracket can be advantageously employed in tomosynthesis mammography or conventional mammography.

In one embodiment, the side-walls of the compression paddle are inclined at an angle with respect to the paddle base so as to provide the x-ray beam with uninterrupted access to the object of interest when a central axis of the x-ray beam is inclined at an angle of up to about 75 degrees with a vertical line drawn at the inner surface of the side walls. The inclination of the side-walls with respect to the paddle base 12 is termed angulation. In another embodiment, the height of the side-walls is reduced from the height employed in other commercially available compression paddles thereby once again providing the x-ray beam with interrupted access to an object of interest when the central axis of the x-ray beam is inclined at an angle of up to about 75 degrees with a vertical line drawn at the inner surface of the side walls. Both of these advantageous side-wall features may be combined in a single compression paddle if desired.

As noted above, the compression paddle may be fixedly attached or matingly engaged to a bracket that is rotatably pivoted about the selected position on the x-ray device. The bracket comprises arms that contact the side-walls of the compression paddle to provide the paddle with support when it is raised or lowered onto an object of interest. In one embodiment, the arms of the bracket are angulated and reduced in height so as to allow the x-ray beam uninterrupted access to the object of interest, when the central axis of the x-ray beam is inclined at an angle of up to about 75 degrees with a vertical line drawn at the inner surface of the arms. The bracket can be fixedly attached to a transparent sheet at its base to compress the object of interest. In one embodiment, a bracket that has angulated arms and/or reduced height arms can be advantageously used to replace a compression paddle with angulated side-walls.

Figure 2:
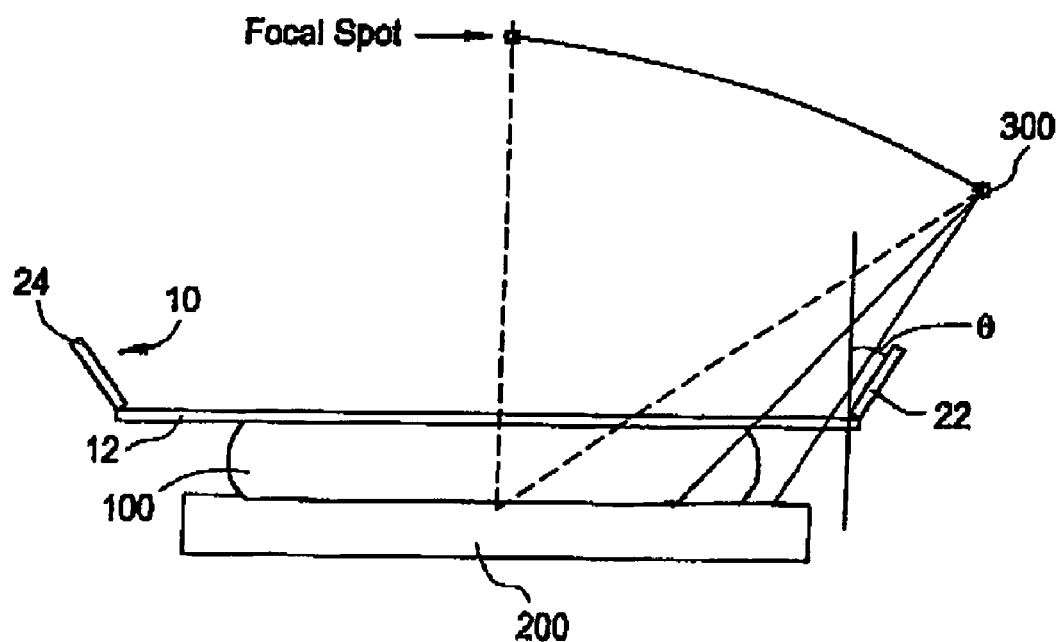
FIG. 2 is a schematic depiction illustrating that a compression paddle 10 with suitably angulated side-walls 22, 24 does not obstruct the x-rays during imaging.

With reference now to the FIGS. 2 and 3, a compression paddle 10 comprises a paddle wall 20 that comprises a first side-wall 22, a second side-wall 24, a back-wall 26, and a front-wall 28. The first side-wall 22 and the second side-wall 24 each have inner surfaces 32 and 34 respectively that face each other, while the back-wall 26 and the front-wall 28 have inner surfaces 36 and 38 respectively that face each other. The inner surface refers to those surfaces that face each other, while the outer surface refers to those surfaces that are on the opposite side of an inner face of a side-wall.

Each side-wall also comprises a lower surface and an upper surface. The upper surface refers to those surfaces that face the x-ray source 300. The lower surface refers to those surfaces that face the object of interest. The object of interest is generally a breast. The side-walls along with the front and back-wall are fixedly attached or matingly engaged to the paddle base 12. The upper surfaces of the side-walls may contact a bracket (not shown) if desired. Optionally, the upper surfaces of the front and back-wall may contact the bracket if desired. The first and second side-walls 22 and 24 are disposed on the upper surface, but on opposing edges of the paddle base 12 respectively, while the back and the front-walls 26 and 28 are also disposed on the upper surface, but on opposing edges of the paddle base respectively. The bottom most inner edge of each side-wall (i.e., the inner edge of the lower surface of each side-wall) is arranged to be perpendicular to the bottom most inner edge of an adjacent front or back-wall. The bottom most inner edge of each side-wall contacts the paddle base 12. Thus, for example, the bottom most inner edge of the first side-wall 22 is perpendicular to the bottom most inner edges of the back and front-walls 26 and 28 respectively.

The back-wall 26 is generally in mechanical communication with a bracket (not shown) that is pivotably disposed on the x-ray device, while the front-wall 28 generally contacts the chest of the patient being examined. The front-wall of the compression paddle 10 is therefore often termed the "chest wall".

In an exemplary embodiment depicted in the FIG. 2, the first side-wall 22 and the second side-wall 24 have their respective facing surfaces 32 and 34 inclined at an angle θ with respect to the vertical to the paddle base 12. The inclination of the facing surfaces 32 and 34 is selected to prevent the first and second side-walls 22 and 24 from obstructing the x-ray beam during imaging of an object of interest. In one embodiment, the angulation of the facing surfaces 32 and 34 can be varied depending upon the maximum angle desired for imaging during tomo-acquisition. Tomo-acquisition includes collecting imaging data during tomosynthesis. The x-ray beam therefore has uninterrupted access to the object of interest (e.g., the breast).

As noted above, the angulation of the facing surfaces 32 and 34 can be varied depending upon the maximum angle desired for tomoacquisition. In one embodiment, the angle θ can vary in an amount of 15 degrees to 75 degrees on both sides of a perpendicular to the paddle base, i.e., a vertical line. The vertical line is preferably drawn at the inner edge of the first or second sidewalls. Thus, the x-ray source (e.g., an x-ray tube) can be tilted to a maximum angle of 75 degrees while imaging an object without any obstruction of the x-ray beam by the respective walls. The ratio of the height of the sidewall to the length of the base is about 1:50 to 1. In one embodiment, the ratio of the height of the sidewall to the length of the base is about 1:15 to 1:2. In another embodiment, the ratio of the height of the sidewall to the length of the base is about 1:10 to 1:3. Exemplary ratios of the height of the sidewall to the length of the base is about 1:15 when θ is about 30 degrees, about 1:14 when θ is about 25 degrees, 1:13 when θ is about 20 degrees, or 1:12.5 when θ is about 15 degrees.

The back-wall 26 and the front-wall 28 are disposed upon the paddle base 12 in a manner such that their respective inner surfaces 36 and 38 are preferably vertical with respect to the upper surface of the paddle base 12. In one embodiment, the front-wall 28 can have a vertical height that exceeds the vertical height of the first side-wall 22 or the second side-wall 24. This will be referred to as an "increased height front-wall". This is depicted in the FIG. 3, where the height of the front-wall 28 is greater than the height of the first side-wall 22 or the second side-wall 24. This increased height of the front-wall 28 facilitates the exclusion of any breast tissue from being directly illuminated by the x-ray beam.

In yet another exemplary embodiment depicted in the FIG. 4, the height of the first side-wall 22 and the height of the second side-wall 24 is reduced to an amount that prevents obstruction of the x-ray beam when the central axis of the beam is inclined at an angle of greater than or equal to about 15 degrees to the vertical. The x-ray beam can be inclined at an angle of up to 75 degrees to the vertical. In this embodiment, the first and second side-walls 22 and 24 are not inclined at an angle, but are disposed vertically on the paddle base 12. Side-walls having reduced heights will hereinafter be referred to as "reduced height side-walls".

In one embodiment, the height of the first side-wall 22 and/or the height of the second side-wall 24 is reduced to an amount that prevents obstruction of the x-ray beam when the central axis of the beam is inclined at an angle of greater than or equal to about 30 degrees to the vertical. In another embodiment, the height of the first side-wall 22 and/or the height of the second side-wall 24 is reduced to an amount that prevents obstruction of the x-ray beam when the central axis of the beam is inclined at an angle of greater than or equal to about 45 degrees to the vertical. In yet another embodiment, the height of the first side-wall 22 and/or the height of the second side-wall 24 is reduced to an amount that prevents obstruction of the x-ray beam when the central axis of the beam is inclined at an angle of greater than or equal to about 60 degrees to the vertical.

As noted above, the ratio of the height of the sidewall to the length of the base is about 1:50 to 1. In one embodiment, the ratio of the height of the sidewall to the length of the base is about 1:15 to 1:2. In another embodiment, the ratio of the height of the sidewall to the length of the base is about 1:10 to 1:3. Exemplary ratios of the height of the sidewall to the length of the base is about 1:15 when θ is about 30 degrees, about 1:14 when θ is about 25 degrees, 1:13 when θ is about 20 degrees, or 1:12.5 when θ is about 15 degrees.

Figure 5:
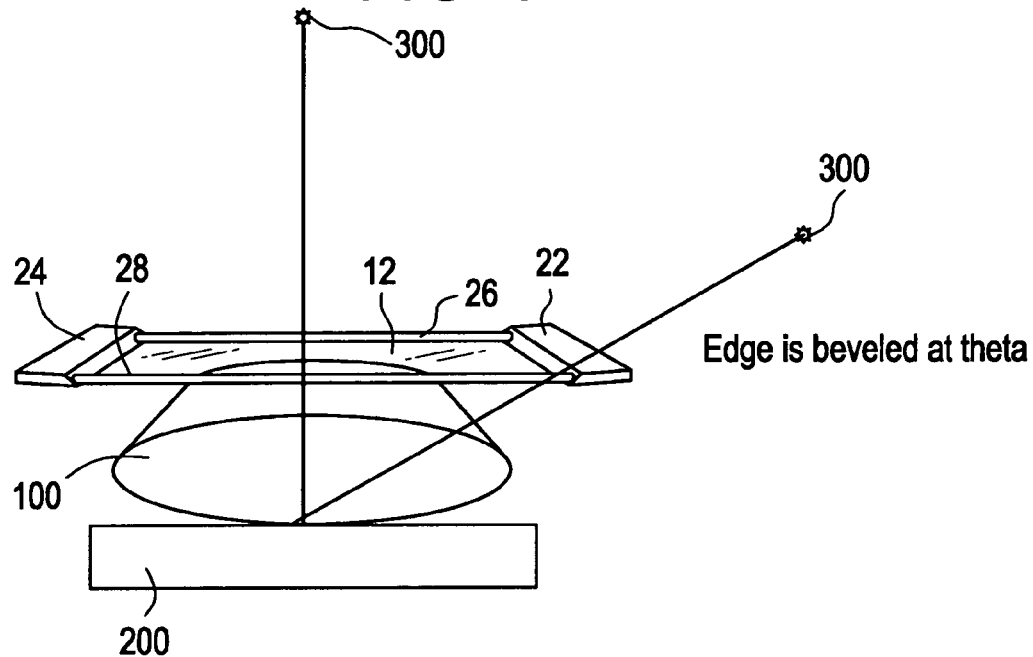
FIG. 5 depicts a compression paddle 10 having angulated side-walls with a shorter steel section and employing a tensioned membrane or plate as the paddle base 12.
Figure 6:
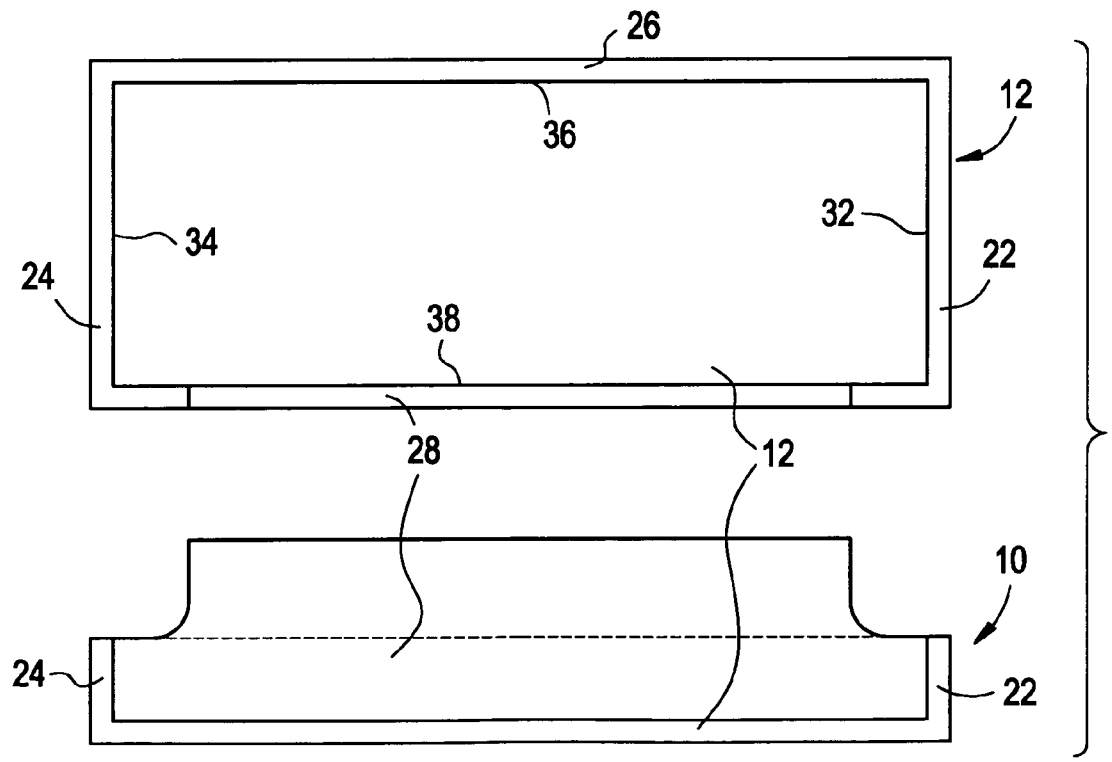
FIG. 6 is a depiction of a plan view and a side view of an exemplary compression paddle 10 that comprises reduced height side-walls 22, 24 and an increased height chest wall 28.

In one embodiment, it may be desirable for the compression paddle to have various combinations of the above-mentioned embodiments. For example, it may be desirable for the compression paddle to have a first side-wall 22 that is inclined at an angle to the paddle base, with a reduced height second side-wall 24 or vice versa. In another embodiment, it may be desirable for the compression paddle to have reduced height first and second sidewalls 22 and 24 while having an increased height front-wall 28. In yet another embodiment, depicted in the FIG. 5, it may be desirable to have reduced height side-walls that are inclined. In the FIG. 5, the side-walls 22 and 24 as well as the front and back-walls 28 and 26 respectively are of a reduced height and have angulated upper surfaces or edges that do not interrupt access of the x-ray beam to the object on interest. FIG. 6 reflects a compression paddle that comprises reduced height side-walls 22, 24 and an increased height front-wall 28.

The paddle walls 20 of the compression paddle 10 are generally manufactured from metals or from radiolucent materials. Exemplary metals are steel, aluminum, magnesium, or the like, or a combination comprising at least one of the foregoing metals. For example in the FIG. 5, the paddle walls 20 can be manufactured from a steel section while using a tensioned membrane or a plate as the paddle base 12. In one embodiment, only the paddle walls 20 of the paddle is manufactured from aluminum.

The radiolucent materials generally comprise polymeric resins. The polymeric resins may be thermoplastic resins, thermosetting resins, or a combination comprising at least one of the foregoing resins. Examples of suitable thermoplastic resins are polyolefins, polyesters, polycarbonates, polyphenylene ethers, polyetherimides, polyamides, polyvinylchlorides, polyacrylates, polymethacrylates, or the like, or a combination comprising one of the foregoing polymers. Examples of suitable thermosetting resins are polyurethanes, epoxy, phenolic resins, or the like, or a combination comprising at least one of the foregoing resins. Carbon fibers or graphite fibers are generally used to reinforce the polymeric resins. When carbon fibers or graphite fibers are used to reinforce the polymeric resins, the resulting side-walls, the front and back-walls are radiolucent composites.

An exemplary paddle is one having an aluminum frame or a radiolucent graphite composite frame.

As noted above, the compression paddle 10 also comprises a paddle base 12. The paddle base 12 is fixedly attached to the respective paddle-walls 20. It is generally desirable for the paddle base 12 to be optically transparent. Examples of suitable optically transparent polymeric resins that can be used as the paddle base 12 are polycarbonate, polymethylmethacrylate, polymethylpentene, polystyrene, or the like, or a combination comprising at least one of the foregoing transparent polymeric resins.

In one exemplary embodiment, the paddle base 12 comprises a tensioned sheet or a plate manufactured from polymethylpentene commercially available as TPX® from Mitsui Chemicals. In another exemplary embodiment, the paddle base 12 comprises a tensioned sheet or a plate manufactured from polycarbonate commercially available as LEXAN® from General Electric Corporation. The thickness of the sheet that is employed as the paddle base 12 is about 0.125 millimeters to about 5 millimeters. In one embodiment, the thickness of the sheet employed as the paddle base 12 is about 0.200 millimeters to about 4 millimeters. In another embodiment, the thickness of the sheet employed as the paddle base 12 is about 0.500 millimeters to about 3 millimeters. In an exemplary embodiment, the thickness of the sheet employed as the paddle base 12 is about 2.5 millimeters.

As noted above, the compression paddle 10 can be raised or lowered by means of bracket 40 that is rotatably pivoted about a selected point on the x-ray device. The bracket 40 has arms 42 to provide mechanical support to the compression paddle 10 and permit the compression paddle 10 to be raised or lowered to accommodate the object of interest. In one embodiment, the bracket 40 has arms 42 that contact the entire perimeter of the compression paddle 10 at the upper surface of the paddle wall 20. In another embodiment, the bracket 40 has arms 42 that contact the upper surface of the paddle wall 20 over a length that exceeds half of the perimeter of the paddle wall 20. In yet another embodiment, the bracket 40 has arms 42 that contact the upper surface of the paddle wall 20 over a length that exceeds half of the length of each of the side-walls 22 and 24 respectively. The perimeter of the paddle wall 20 is the total length of the upper surface of the first and second side-walls 22, 24, as well as the upper surface of the back-wall 26 and the front-wall 28.

As noted above, in one embodiment, the compression paddle 10 is fixedly attached to a bracket that is rotatably pivoted about a selected point on the x-ray device. The bracket provides support to the compression paddle 10. With reference now to the FIG. 7, the bracket 40 comprises a first arm 46 and a second arm 48 both of which extend from a central portion 44. The central portion 44 is rotatably pivoted about a selected point on the x-ray device. Each arm has an inner surface 52, an outer surface 54, and an upper surface 56. Each arm 46, 48, further comprises a groove 50 that permits the compression paddle 10 (not shown) to be in operative communication with the bracket 40. As depicted in the FIG. 7, the groove 50 is located on the inner surface 52. Thus the compression paddle 10 can be displaced in conjunction with the bracket 40. For example, when the bracket 40 is displaced upwards, away from the detector, the compression paddle 10 is also displaced upwards away from the detector.

FIG. 8 depicts a bracket 40 comprising a first arm 46 and a second arm 48 that contacts the upper surface of a compression paddle 10 having angulated side-walls 22 and 24. In this depiction, the first and second arms 46, 48, contact the upper surface of the side-walls 22 and 24 for over half of a length of each side-wall. This provides support to the side-wall during a displacement or during tomoacquisition. In one embodiment depicted in the FIG. 8, the groove 50 contacts the upper surfaces and/or the outer surfaces of the paddle walls 20 of the compression paddle 10 in a tight fit and establishes frictional communication with the compression paddle 10. This frictional communication enables the bracket 40 to support the compression paddle 10 and permits the compression paddle 10 to be raised or lowered with the bracket 40. The groove 50 may be located on any desirable surface of the bracket 40 such as the inner surface 52, the outer surface 54 and/or the upper surface 56. In an exemplary embodiment, the groove 50 is located on the lower portion (i.e., on the portion facing the detector) of the inner surface 52 of the arms 46, 48.

Figure 9:
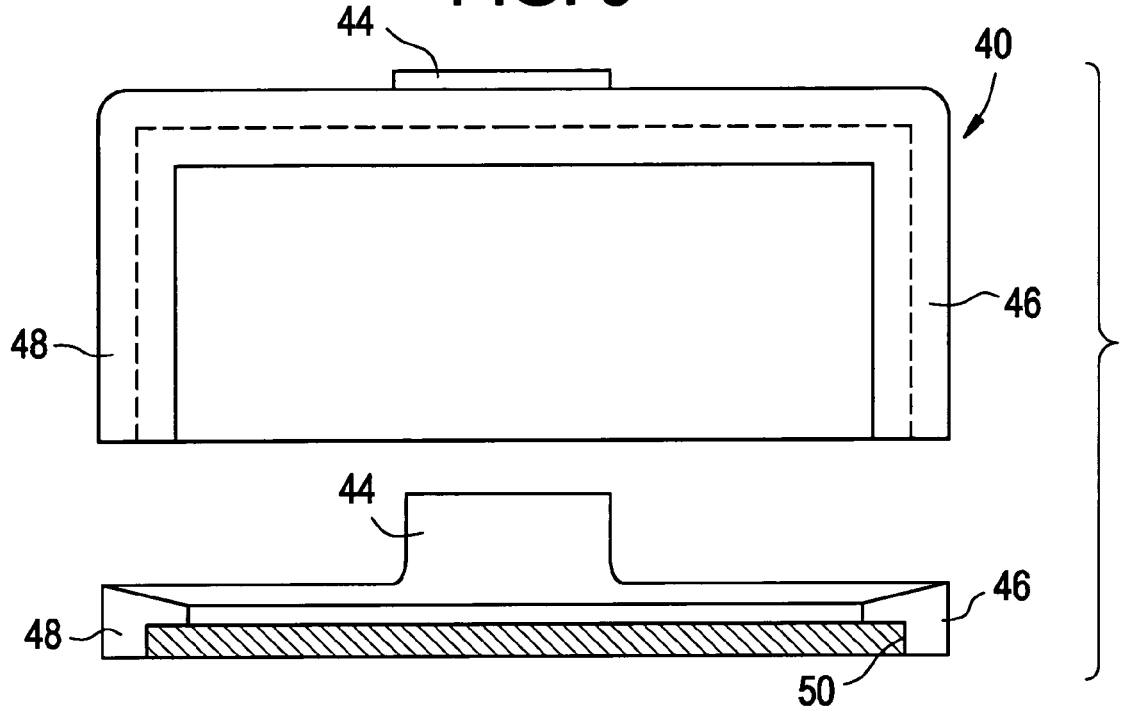
FIG. 9 is a depiction of an exemplary bracket 40 contacting a compression paddle 10, wherein a tight fit between the groove 50 and the outer surface of the compression paddle 10 maintains the compression paddle 10 in position.
Figure 10:
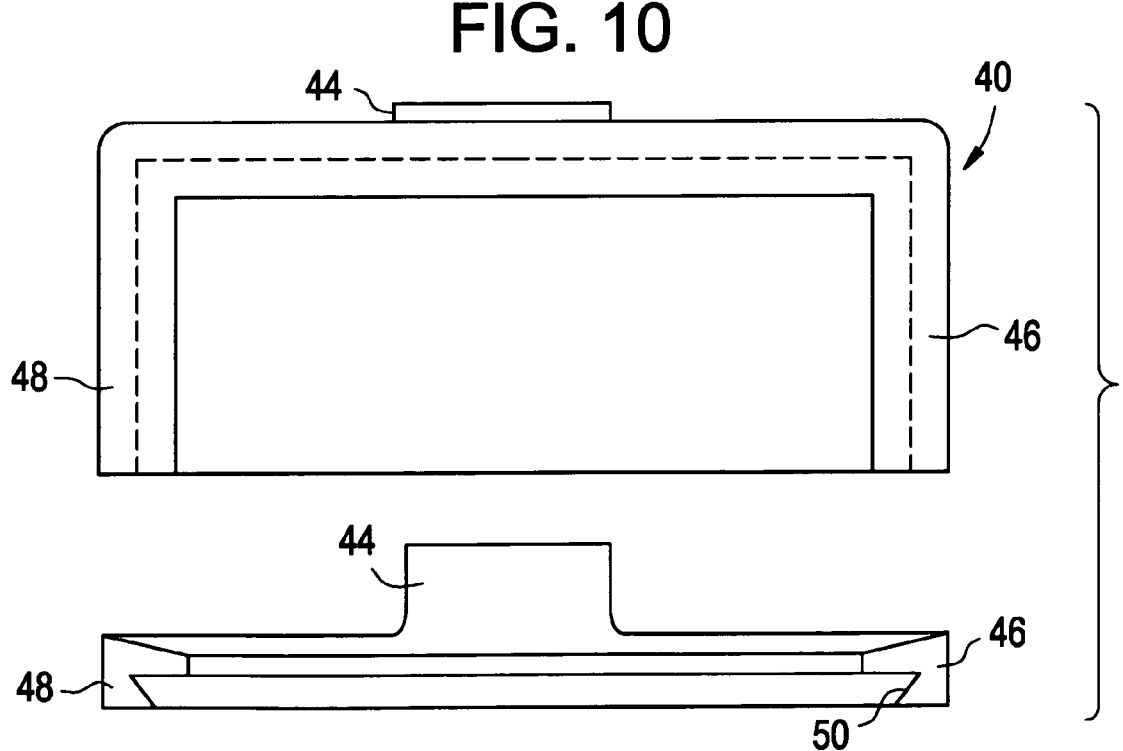
FIG. 10 is a depiction of an exemplary bracket 40 contacting a compression paddle 10, wherein a dove tail joint between the groove 50 and the outer surface of the compression paddle 10 maintains the compression paddle 10 in position.

In yet another embodiment depicted in the FIG. 8, 9 or 10, the groove 50 may have a shape that permits it to mate with an opposing shape located on the outer surface of the compression paddle 10 or the paddle base 12. For example, the bracket 40 and the compression paddle 10 can be fixedly attached to each other by a dove tail joint, a mitre joint, a bridle joint, a scarf joint, a half-lap joint, a butt joint, an edge joint, a mortise and tenon joint, or the like, or a combination comprising at least one of the foregoing joints. For example in the FIG. 8 the angulated upper surface of the compression paddle 10 mates with a wedge shaped inner surface 52 of the groove 50, which facilitates the attachment of the compression paddle 10 with the bracket 40.

In the FIG. 9, a compression paddle 10 that has a flat upper surface is fixedly attached into the groove 50 of the bracket 40. The friction between the inner surface of the groove 50 and the outer surface of the compression paddle 10 maintains the compression paddle 10 in position during tomoacquisition. In FIG. 10, a compression paddle 10 comprising a flat upper surface and a beveled edge is fixedly attached to the bracket 40 by using a mating joint.

In yet another embodiment, the bracket 40 can be fixedly attached to the paddle walls 20 by means of clamps, screws, rivets, adhesives, or the like.

Returning now to the FIGS. 7 and 8, the upper surfaces 56 of the first arm 46 and the second arm 48, (i.e., the surface that faces the x-ray source 300), may be angulated (beveled) to eliminate obstructions to the incident x-ray beam. In one embodiment, the amount of beveling is effective to prevent obstruction to the x-ray beam, when the central axis of the x-ray beam is inclined at an angle of up to about 75 degrees with a vertical (perpendicular) to the paddle base 12 when the vertical is drawn at the inner surface 52 of the arms of the bracket. In another embodiment, the amount of angulation is effective to prevent obstruction to the x-ray beam, when the central axis of the x-ray beam is inclined at an angle of up to about 60 degrees with a vertical to the paddle base 12 drawn at the inner surface 52 of the arms of the bracket. In yet another embodiment, the amount of angulation is effective to prevent obstruction to the x-ray beam, when the central axis of the x-ray beam is inclined at an angle of up to about 45 degrees with a vertical to the paddle base 12 drawn at the inner surface 52 of the arms of the bracket. In yet another embodiment, the amount of angulation is effective to prevent obstruction to the x-ray beam, when the central axis of the x-ray beam is inclined at an angle of up to about 30 degrees with a vertical to the paddle base 12 drawn at the inner surface 52 of the arms of the bracket. In yet another embodiment, the amount of angulation is effective to prevent obstruction to the x-ray beam, when the central axis of the x-ray beam is inclined at an angle of up to about 15 degrees with a vertical to the paddle base 12 drawn at the inner surface 52 of the arms of the bracket.

The angulation of the upper surface 56 of the bracket 40 is varied in an amount of about 15 degrees to about 75 degrees with a perpendicular drawn to the paddle base 12. In one embodiment, the beveling is varied in an amount of about 30 degrees to about 60 degrees with a perpendicular line drawn to the paddle base 12. In yet another embodiment, the beveling is varied in an amount of about 35 degrees to about 45 degrees with a perpendicular line drawn to the paddle base 12.

As noted above, it is generally desirable for the first arm 46 and the second arm 48 of the bracket 40 to contact the upper surface of the paddle wall 20 over a length that is greater than half of the perimeter of the upper surface of the paddle wall 20. As noted above, the upper surface refers to that surface that faces the x-ray source 300. The first arm 46 and the second arm 48 may therefore be open ended (i.e., they do not contact each other) as seen in the FIGS. 7 and 8. Alternatively the first arm 46 and the second arm 48 may contact each other at a point opposite the central portion 44 of the bracket 40 as shown in the FIGS. 11 and 12. When the first arm 46 contacts the second arm 48, it is generally desirable for the bracket 40 to contact the upper surface of the paddle wall 20 along the entire perimeter.

Figure 11:
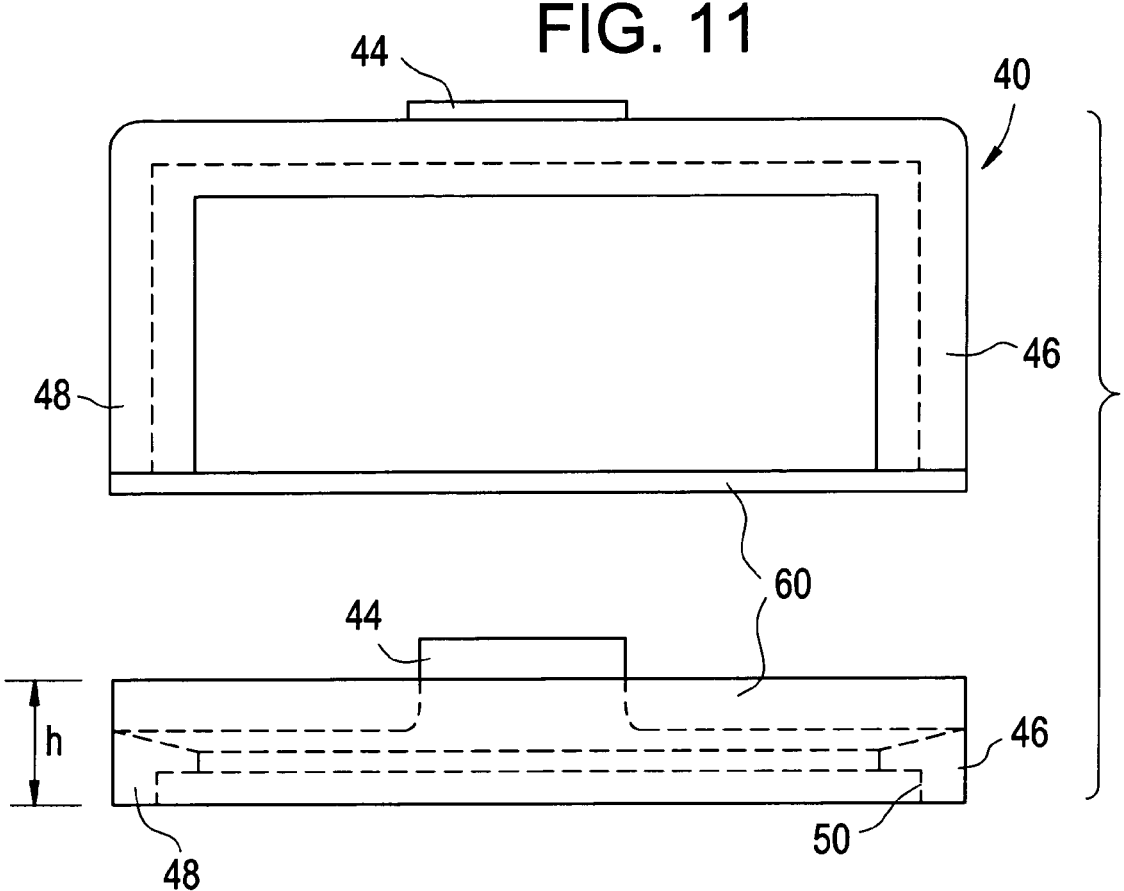
FIG. 11 is a depiction of plan view and a side view of an exemplary bracket 40 having a high chest wall.
Figure 12:
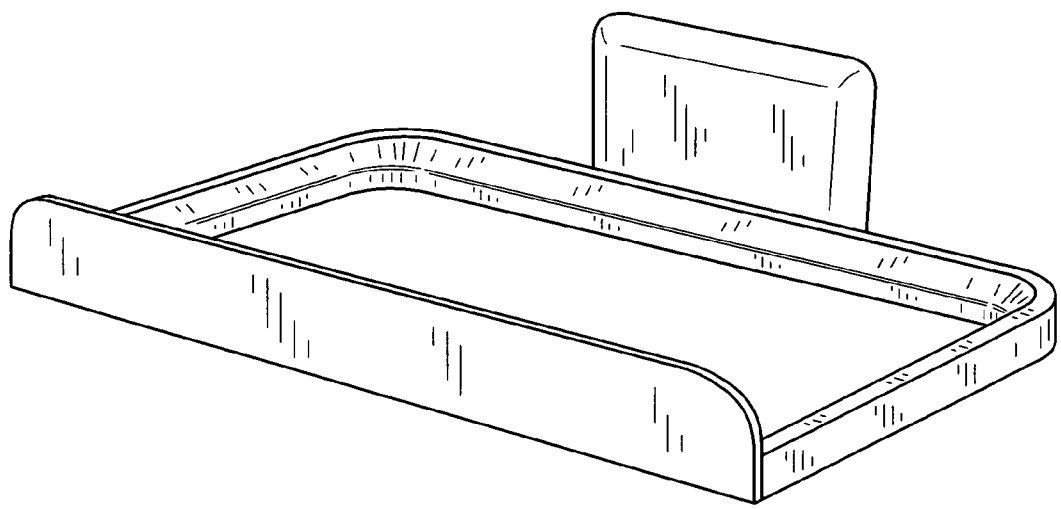
FIG. 12 is an exemplary perspective view of the bracket 40 having a high chest wall.

In one embodiment, the portion 58 of the bracket 40 that is opposed to the central portion 44 may comprise a chest wall 60 as depicted in the FIGS. 11 and 12. In other words, the first arm 46 and the second arm 48 are in communication with each other via the chest wall 60. The chest wall 60 acts a barrier to prevent tissue from being exposed to x-rays. The chest wall 60 may have a height "h" of about 1 centimeter to about 10 centimeters from the base of the bracket 40. In one embodiment, the chest wall 60 may have a height "h" of about 2 centimeters to about 8 centimeters from the base of the bracket 40. In another embodiment, the chest wall 60 may have a height "h" of about 3 centimeters to about 7 centimeters from the base of the bracket 40.

The compression paddle 10 as well as the bracket 40 disclosed herein permit tomoacquisitions at wide angles of up to 60 degrees with any interruptions or obstructions between the x-ray beam and the object of interest. This permits improved spatial differentiation of nearby tissues at very high resolution. The ability to make tomoacquisitions at wide angles also reduces the need for correcting images that contain shadows thereby improving the speed of the process.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A compression paddle comprising:
   a paddle base and
   a paddle wall comprising:
   a first side-wall;
   a second side-wall; wherein the first side-wall or the second side-wall are disposed upon the paddle base and inclined with respect to the paddle base at an angle that is effective to permit an x-ray beam from an x-ray source uninterrupted access to an object of interest, said object located on an opposing side of the paddle base from the x-ray source, wherein an angle between a central axis of the x-ray beam and a vertical to the paddle base taken at an inner surface of the first side-wall or an inner surface of the second side-wall is about 15 degrees to about 75 degrees; and
   bracket, wherein the bracket comprises a groove for fixedly attaching or matingly engaging the compression paddle; a first arm; and a second arm; each arm having the groove disposed therein; wherein the first arm and the second arm extend from a central portion of the bracket, and wherein the first arm and the second arm comprise angulated upper surfaces that permit an x-ray beam from an x-ray source uninterrupted access to an object of interest, said object located on an opposing side of the paddle base from the x-ray source, wherein an angle between a central axis of the x-ray beam and a vertical to the paddle base taken at an inner surface of the first arm or the inner surface of the second arm is about 15 degrees to about 75 degrees.

2. A compression paddle for use with an x-ray source comprising:
   a paddle base and
   a paddle wall comprising:
   a first side-wall; and
   a second side-wall; wherein the first side-wall or the second side-wall are disposed upon the paddle base and inclined with respect to the paddle base at an angle that is effective to permit an x-ray beam from the x-ray source uninterrupted access to an object of intersst, said object located on an opposing side of the paddle base from the x-ray source, wherein an angle between a central axis of the x-ray beam and a vertical to the paddle base taken at an inner surface of the first side-wall or an inner surface of the second side-wall is about 15degrees to about 75 degrees;
   a bracket, wherein the bracket comprises a groove for fixedly attaching the compression paddle; a first arm; and a second arm; each arm havina the groove disposed therein; wherein the first arm and the second arm comorise anaulated uooer surfaces that permit the x-ray beam uninterrupted access to the ebiect of interest.

3. A compression paddle for use wilh an x-ray source comprising:
   a paddle base and
   a paddle wall comprising:
   a first side-wall; and
   a second side-wall; wherein the first side-wall or the second side-wall are disposed upon the paddle base and inclined with respect to the paddle base at an angle that is effective to permit an x-ray beam from the x-ray source uninterrupted access to an object of interest, said object located on an opposing side of the paddle base from the x-ray source,
   a bracket, wherein the bracket comprises a grooye for fixedly attaching the compression paddle; a first arm; and a second arm; each arm having the groove disposed therein; wherein the first arm and the second arm comprise angulated upper surfaces that permit the x-ray beam uninterrupted access to the object of interest.

4. A compression paddle comprising:
   a paddle base; and
   a paddle wall compnsing:
   a first side-wall; and a second side-wall; wherein the first side-wall and the second side-wall are disposed upon the paddle base and have a height that is effective to permit an x-ray beam from an x-ray source uninterrupted access to an object of interest, said object located on an opposing side of the paddle base from the x-ray source, wherein an angle between a central axis of the x-ray beam and a vertical to the paddle base taken at an inner surface of the first side-wall or the inner surface of the second side-wall is about 30 degrees to about 60 degrees; and a bracket, wherein the bracket comprises a groove for fixedly attaching the compression paddle; a first arm; and a second arm; each arm having the groove disposed therein; wherein the first arm and the second arm extend from a central portion of the bracket, and wherein the first arm and the second arm comprise angulated upper surfaces that permit an x-ray beam uninterrupted access to an object of interest located on an opposing side of the paddle base from an x-ray source when an angle between a central axis of the x-ray beam and a vertical to the paddle base taken at an inner surface of the first arm or the inner surface of the second arm is about 30 degrees to about 60 degrees.

5. A bracket for use in an x-ray device comprising:
a groove for fixedly attaching a compression paddle;
a first arm; and
a second arm; each having the groove disposed therein; wherein the first arm and the second arm extend from a central portion of the bracket, and wherein the first arm and the second arm comprise angulated upper surfaces that permit an x-ray beam from an x-ray source uninterrupted access to an object of interest, said object located on an opposing side of the paddle base from the x-ray source, wherein an angle between a central axis of the x-ray beam and a vertical to the paddle taken at an inner surface of the first arm or the inner surface of the second arm is about 30 degrees to about 75 degrees.

6. The bracket of claim 5, wherein the angle between a central axis of the x-ray beam and a vertical to the paddle taken at an inner surface of the first arm or the inner surface of the second arm is about 30 degrees to about 60 degrees.

7. The bracket of claim 5, wherein the bracket is rotatably pivotable about the x-ray device.

8. The bracket of claim 5, wherein the groove provides frictional communication between the compression paddle and the bracket.

9. The bracket of claim 5, wherein the first arm and the second arm have a height that permits an x-ray beam uninterrupted access to an object of interest located on an opposing side of the paddle base from an x-ray source when an angle between a central axis of the x-ray beam and a vertical to the paddle taken at an inner surface of the first arm or the inner surface of the second arm is about 30 degrees to about 60 degrees.

10. An x-ray device having the bracket of claim 5.

* * * * *